United States Patent [19]

Wood

[11] Patent Number: 4,912,136

[45] Date of Patent: Mar. 27, 1990

[54] USES OF A SUBSTITUTED 2-PHENOXYPHENYLACETIC ACID AS AN IMMUNOSUPPRESSANT DRUG

[76] Inventor: Elizabeth M. Wood, Lubnaig, 442 Blackness Road, Dundee, United Kingdom, DD2 1TQ

[21] Appl. No.: 212,915

[22] Filed: Jun. 29, 1988

[30] Foreign Application Priority Data

Jun. 29, 1987 [GB] United Kingdom ................ 8715242

[51] Int. Cl.[4] ............................................. A61K 31/19
[52] U.S. Cl. .................................................... 514/557
[58] Field of Search ........................................ 514/557

[56] References Cited

FOREIGN PATENT DOCUMENTS 1308327 2/1973 United Kingdom .

OTHER PUBLICATIONS

Dunagan, F. M. et al, "Quantitation of Dose and Concentration-Effect Relationships for Fenclofenac in Rheumatoid Arthritis", Br. J. Clin. Pharmac. (1986), 21, 409-416.

Katona, G., "Fenclofenac: A New Nonsteroidal Antiinflammatory Drug with an Immunomodulatory Effect in The Treatment of Active Rheumatoid Arthritis", Current Therapeutic Research, vol. 37, No. 1, Jan. 1985, pp. 58-69.

Atkinson et al, Agents & Actions, 6,(5), 657-666 (1976) Anti-Inflammatory and Related Properties of 2-(2-,3-dichlorophenoxy) Phenylacetic Acid (Fenclofenac).

Phillips, N. C., "Immuno-Inflammatory Pharmacology of Fenclofenac: A Preliminary Report", Royal Society of Medicine, Series No. 28, 1980, pp. 83-88, Academic Press and Grune and Stratton, London.

Matheus, P. C. et al, Brazilian Congress of Rheumatology, Recife, Jul. 1982, reported in Rev. Bras. Reumat. 22 (3) 139 (1982), "The Effect of Fenclofenac on Cellular Immunity".

Ku, E. C. et al, "The Effects of Diclofenac Sodium on Arachidonic Acid Metabolism", Seminars in Arthritis and Rheumatism, 15, 2, Suppl. 1, 36-41 (1985).

Primary Examiner—Stanley J. Friedman
Attorney, Agent, or Firm—Florence U. Reynolds

[57] ABSTRACT

Although fenclofenac (2-(2,4-dichloro-phenoxy) phenyl acetic acid) is known as an NSAID it has now been shown to have immunosuppressive properties indicating its usefulness in the treatment of a wide variety of conditions requiring immunosuppressive therapy. In this role fenclofenac may be combined with a prostaglandin and/or another immunosuppressive drug, and may be administered in a form for release in the terminal ileum or colon.

5 Claims, 8 Drawing Sheets

USES OF A SUBSTITUTED 2-PHENOXYPHENYLACETIC ACID AS AN IMMUNOSUPPRESSANT DRUG

BACKGROUND OF THE INVENTION (1) Field of the invention

This invention relates to the uses of fenclofenac (2-(2,4-dichloro-phenoxyphenylacetic) acid as an immunosuppressant drug.

(2) Description of the prior art

A non-steroidal anti-inflammatory drug (NSAID) relieves the symptoms of the disease for which it is prescribed. All NSAIDs inhibit the enzyme cyclooxygenase and therefore decrease the production of prostaglandins and thromboxane A2. This effect is thought to be responsible for the alleviation of the symptoms due to inflammation, especially in diseases such as rheumatoid arthritis for which they are principally prescribed. Fenclofenac, which is described and claimed in the specification of British Patent No. 1308327, is an example of an NSAID which was marketed for many years for the treatment of rheumatoid arthritis.

Some NSAIDs also inhibit lipoxygenases and may reduce local inflammation and polymorphonuclear leucocyte activation by inhibition of leukotriene B4.

Prostaglandin inhibition is also thought to be responsible for the adverse effects of NSAIDs on the gastrointestinal tract—an unwanted side effect of these drugs. However these side effects are easier to manage than those due to steroid therapy and to other immunosuppressive drugs which are needed to treat severe disease and to modify the disease process.

In rheumatoid arthritis the synovial membranes of the joints are involved in an intense cellular infiltration. The infiltrating cells are lymphocytes, plasma cells and macrophage-like cells. Polymorphonuclear leucocytes (neutrophils) are scanty o absent in the membrane but plentiful in the synovial fluid in the joint cavity. 80% of the lymphocytes present in the rheumatoid synovial membrane are T cells and 20% are B cells. Of the T cells present the ratio of T-helper to T-suppressor cells is in the order of 10:1 compared with 2:1 in normal lymph nodes or blood. The role of synovial lymphocytes in the pathogenesis of rheumatoid arthritis has been established by the thoracic duct drainage studies of Paulus et al., which showed improvement of the disease following removal of thoracic duct lymphocytes and, in selected cases, flare-up of the disease on reinfusion. Studies using lymphopheresis have confirmed the improvement in the disease of rheumatoid arthritis after removal of lymphocytes from the peripheral blood.

There is some evidence from experimental animal studies that fenclofenac is more effective than other non-steroidal anti-inflammatory drugs in inhibiting chronic immunologically mediated inflammation than in alleviating acute irritant-induced inflammation [Atkinson, D. C. and Leach, E. C. *Agents and Actions*, 6, (5), 657-666 (1976)]. In a preliminary study on the immunoinflammatory pharmacology of fenclofenac Philips, N. C. [*Fenclofenac in Arthritis An International Symposium* (eds. Swain, M. C. and Goldberg, A. A. J.) Royal Society of Medicine, pp. 83-88 (1980)] shows that fencloenac is not active during the initial humoral phase of a delayed type hypersensitivity reaction in mice but is active during the later phase. Although the other drugs tested, such as diclofeac and indomethacin, had an even greater effect during the later stages, and an effect greater than that of fenclofenac, and although none of the compounds tested (with the exception of cyclophosphamide which was included as a known immunomodulator) was found to have any significant effect on the percentage of T- and B-lymphocytes, Philips nevertheless draws the conclusion that fenclofenac may be acting specifically at a more fundamental level in inhibiting immunologically mediated inflammation than a number of other non-steroidal anti-inflammatory drugs.

In an abstract [Rev. Bras. Reumat 22(3), 139 (1982)] of a paper to be given at the Brazilian Congress of Rheumatology, Recife, in July 1982, Matheus P. C. et al. followed a previous suggestion that fenclofenac has the capacity to induce remissions in the natural evolution of rheumatoid arthritis by observing the effect of fenclofenac on the function of neutrophils, monocytes and lymphocytes.

In view of the incompleteness of the report, in particular with respect to dose responses, and to a definition of "physiological concentrations of fenclofenac", it is difficult to appreciate the statistical significance of the low blastic transformation counts; the two earlier papers to which reference is made for a description of the techniques employed lack such a description for the blastic transformation of lymphocytes. It is consequentially difficult to evaluate the authors' assertion that fenclofenac proved to be a powerful inhibitor of the function of lymphocytes. The author's eventual conclusion from their work is limited to the suggestion that fenclofenac may be of real value in the treatment of long term rheumatoid arthritis.

BRIEF SUMMARY OF THE INVENTION

Investigations on the effect of several NSAIDs on the proliferation of T lymphocytes in vitro were carried out to see if any of them might have a suppressive effect which could alter the disease process in conditions in which proliferation of lymphocytes at the site of the disease process may contribute to the disease process and in hypersensitivity reactions, by limiting the proliferation of T lymphocytes. It was found that fenclofenac, in concentrations equivalent to therapeutic blood levels and diclofenac at the same concentrations suppress the proliferation of T lymphocytes in vitro. The concentrations of fenclofenac which suppress lymphocyte proliferation in vitro are equivalent to therapeutic blood levels and the therapeutic activity is thought to be due to the parent drug. However the concentrations of diclofenac required to suppress lymphocyte proliferation in vitro are 100 times greater than the therapeutic blood levels. Additional studies on fenclofenac showed that the suppressive effect on lymphocytes in vitro is reversible, i.e. the lymphocytes grow normally when the drug is removed. The effect of ortho-chlorophenylacetic acid, the base from which the analogue fenclofenac is derived, on lymphocyte proliferation in vitro has also been tested The concentrations of ortho-chlorophenylacetic acid were the same as fenclofenac in the tissue culture wells and equivalent to therapeutic blood levels. Ortho-chlorophenylacetic acid did not suppress the replicative growth of normal human lymphocytes in vitro at these concentrations.

In vivo studies in animals and man have provided some indirect evidence that fenclofenac may modify the disease process by inhibiting of the delayed type hypersensitivity reaction. The evidence that fenclofenac in concentrations equivalent to therapeutic blood levels may suppress the proliferation of lymphocytes indicates that it may be useful to treat chronic inflammatory diseases and other conditions where immunosuppression is required.

According to the present invention there is provided the use of fenclofenac for the preparation of a medicament with an immunosuppressive action. Such an action may be broadly described as the suppression of hypersensitivity reactions (generally equatable with hypersensitivity types II, III, IV and V) and conditions where proliferation of lymphocytes at the site of the disease process may contribute to the disease process.

In the past fenclofenac has been used principally for the treatment of rheumatoid arthritis but in use according to the present invention as an immunosuppressant it may also be used to treat other conditions n human beings or animals where modification of the immune response or suppression of the proliferation of lymphocytes is required. Such other conditions are now listed beginning with the group of connective tissue diseases, of which rheumatoid arthritis is the most common, and which often require immunosuppressive therapy.

---

Connective tissue diseases
Rheumatoid arthritis
Still's disease
Systemic lupus erythematosus
Progressive systemic sclerosis
Scleroderma
Mixed connective tissue disease
Polymyositis
Dermatomyositis
Diseases of blood vessels
Vasculitis
Polyarteritis nodosa
Auto-immune haematological disorders
Inflammatory bowel disease
Crohn's disease
Ulcerative colitis
Coeliac disease
Chronic active hepatitis
Neurological diseases
Myasthenia gravis
Multiple sclerosis
Guillain Barre syndrome
Skin diseases
Pemphigus
Bullous pemphigoid
Dermatitis herpetiformis
Psoriasis
Auto-immune endocrine diseases
1. Type I Diabetes
   (Juvenile type or insulin dependent)
2. Auto-immune thyroid diseases
   Hashimoto's thyroiditis
   Atrophic hypothyroidism
   Grave's disease
Grave's ophthalmopathy
Idiooathic nephrotic syndrome of childhood
Non-infective uveitis
Reiter's disease
Behcets disease
Sarcoidosis
Tuberculosis and leprosy
Immunosuppression in bone marrow and organ transplantation

---

In tuberculosis and leprosy, it is required to use steroid therapy in addition to specific therapy, to modify the cellular immune response when it causes severe tissue damage and fibrosis the use of fenclofenac according to the present invention would thus be particularly applicable in third world countries where control of steroid therapy may be extremely difficult.

Although in severe and acute phases of all the above-described disease processes, immunosuppression with conventional drugs such as steroids, azathioprine and cyclosporin may be required, for chronic use and for milder cases, fenclofenac may be a suitable drug. Fenclofenac may also be used along with one or more other immunosuppressants to try to reduce the dose of the other drugs and therefore reduce their unwanted side effects.

Even though enclofenac has low ulcerogenic side effects these may be eliminated according to the present invention by presenting the drug for administration in delayed-release form, for example fenclofenac tablets may be coated with an acrylic-based resin (Eudragit F) to ensure release of the active ingredient in the terminal ileum and colon. Alternatively, fenclofenac may be combined with a prostaglandin, preferably any one of the following synthetic analogues of natural prostaglandin E (PGEs): PGE 1 analogue misoprostol; methylated PGE 2 analogues arbraprostil and enprostil; and trimethylated PGE 2 analogue trimoprostil.

When patients are unable to take oral preparations, parental preparations of fenclofenac with pharmaceutically inactive diluents or carriers may be used. A topical preparation of fenclofenac may also be used in skin diseases e.g. psoriasis, the preparation comprising fenclofenac and a suitable carrier, for example ethyl alcohol, or a conventional lotion or cream base.

DESCRIPTION OF THE DRAWINGS

The invention will now be further illustrated by the following non-limiting Examples and with reference to the accompanying drawings in which

FIGS. 5(a)–5(d) are graphs showing the effect of 500 μg/ml fenclofenac on the RNA content of PHA-stimulated lymphocytes from a normal volunteer cultured for 24 h and the DNA content at 72 h measured by flow cytofluorimetry. The solid line is the profile of the PHA-stimulated cells and the interrupted line is that of the unstimulated control cells.

DETAILED DESCRIPTION

GENERAL

Representatives of seven chemical groups of NSAIDs were screened at concentrations equivalent to blood levels in the high therapeutic range and at approximately ten times that concentration to determine and compare their effect on PHA stimulated normal human lymphocytes in vitro The suppression of the growth of phytohaemagglutinin(PHA)-stimulated lymphocytes in vitro by fenclofenac and diclofenac was studied in more detail.

MATERIALS

Stock solutions of all the drugs in the initial screening experiments were made as shown in Table 1. For the more detailed studies, stock solutions were made as follows: fenclofenac (Reckitt and Colman, Hull, England) and diclofenac (Geigy Pharmaceuticals, Horsham, West Sussex, England) were dissolved as 28 mg in 1 ml absolute ethanol and 1 ml sterile distilled water. All the stock solutions were diluted with tissue culture medium, RPMI 1640 (Gibco Bio-cult Ltd., Paisley, Scotland) buffered at pH 7.3 with Hepes and supplemented with L-glutamine (200 nM), penicillin (200 iu/ml) and streptomycin (100 μg/ml), to the appropriate concentration for the addition to the culture wells. The stock solutions in distilled water or alcohol were diluted at lease thirty-five fold in tissue culture medium in the wells. It has been found that distilled water or absolute ethanol diluted thirty-five fold in tissue culture medium has no effect on lymphocyte survival or growth.

In the initial screening tests, the drugs in Table 1 were tested at the concentrations shown in the Table and at ten times these concentrations In the main study, fenclofenac and diclofenac were tested in doubling dilutions over the concentration range 800 μg/ml to 25 μg/ml. Diclofenac was also tested in doubling dilutions over the concentration range 50 μg/ml to 1.25 μg/ml.

TABLE 1

Drugs screened

| Chemical Group | Drug | Source | Stock solution | Concentration in therapeutic range |
|---|---|---|---|---|
| Propionic acid derivatives | Ketoprofen | a | 31.5 mg in 10 ml absolute ethanol | 5 μg/ml |
|  | Fenbufen | b | 47 mg in 16 ml absolute ethanol | 10 μg/ml |
| Pyrrole acetic acid derivatives | Zomepirac | c | 47 mg in 10 ml sterile distilled water | 7 μg/ml |
| Indoleacetic acid derivatives | Sulindac | d | 47 mg in 12 ml absolute ethanol | 6 μg/ml |
|  | Indomethacin | e | 31.5 mg in 10 ml absolute ethanol | 3 μg/ml |
| Anthranilic acid derivatives | Mefenamic acid | f | 31.5 mg in 10 ml absolute ethanol | 5 μg/ml |
| Phenyl acetic acid derivatives | Fenclofenac | g | 28 mg in 1 ml absolute ethanol and 1 ml sterile distilled water | 80 μg/ml |
| Pyrazoles | Azapropazone | h | 17.5 mg in 0.5 ml absolute ethanol | 50 μg/ml |
| Salicylates | Salicylic acid | i | 35 mg in 1 ml absolute ethanol | *300 μg/ml |

*Salicylic acid was tested only at the therapeutic blood level concentration as it was too acidic at 10 times this concentration
Source
a May and Baker Ltd. Dagenham, Essex, England
b Lederle Laboratories, Gosport, Hants., England
c Ortho Pharmaceuticals Ltd., High Wycombe, Bucks., England
d Merck, Sharp and Dohme Ltd., Hoddesdon, Herts., England
e DDSA Pharmaceuticals Ltd., London, England
f Parke, Davies and Co., Pontypool, Gwent, S. Wales
g Reckitt and Colman, Pharmaceutical Division, Hull, England
h A. H. Robins Co. Ltd., Horsham, West Sussex, England
i Sigma Chemical Company, Poole, Dorset, England

TECHNIQUES

Lymphocyte stimulation

Mononuclear cells were separated from heparinised venous blood of healthy volunteers by density gradient centrifugation over Ficoll-Paque (Pharmacia Fine Chemicals, Uppsala, Sweden). The cells were washed three times in tissue culture medium, suspended in tissue culture medium and then cultured in round-bottomed microtitre plates (Sterilin Ltd., Teddington, England). Each well contained 50 μl cell suspension ($4 \times 10^6$/ml), 50 μl drug dilution, 25 μl autologous plasma and 50 μl phytohaemagglutinin (HA16, Welcome Reagents Ltd., Beckenham, England) at an optimum stimulating concentration of 1.14 μg HA16/ml RPMI 1640. The plates were sealed with adhesive tap (Flow Laboratories, Irvine, Scotland) and incubated at 37° C.

Measurement of lymphocyte activation by volume spectroscopy

The cells were harvested after culture for 21–24 h. The cell suspension was measured in an electronic particle counter (Model Fn, Coulter Electronics, Luton, England) and the output accumulated in a multichannel analyser (Channelyzer C1000, Coulter) as previously described (Gibbs, J. H. [*J. Immunol. Methods*, 25, 147–158 (1979)]. The growth during the $G_1$-phase of the first cell cycle was calculated from a comparison of the size distribution profiles of each stimulated culture with that of the corresponding unstimulated control culture. The computer program estimates the best values for the two parameters describing volume-growth of the activated cells as previously described [Gibbs et al., 1979].

Measurement of replicative growth of lymphocytes by liquid scintillation

After culture for 68 h 0.5 μCi tritiated thymidine (Amersham International, Amersham, England) was added to each culture well. The cells were harvested 4 h later with a Skatron harvester (Flow Laboratories, Irvine, Scotland) on filter paper discs. The amount of DNA synthesis was measured by liquid scintillation counting of the air dried discs in NE 233 (Nuclear Enterprises, Edinburgh, Scotland).

The effect of growing lymphocytes with fenclofenac 200 μg/ml for 24 h then washing the cells and reculturing them for a further 48 h was also studied using tritiated thymidine uptake as a measure of replicative growth. The cells were harvested from the wells by Pasteur pipette (as for the volume spectroscopy experiments) into tissue culture medium and were washed twice before they were resuspended in tissue culture medium counted and recultured in a fresh microtitre plate.

Flow cytofluorimetric measurement of cellular nucleic acid content

The resuspended cells from cultures harvested by Pasteur pipette at 24 and 72 h were fixed in 4% neutral buffered formaldehyde and stored in suspension until reading. After centrifugation the supernatant was discarded and the cells were stained with acridine orange (Polysciences Inc., Warrington, PA., USA) by the method of Traganos et al., [*J. Histochem. Cytochem.*, 25, 46–56 (1977)]. DNA content was deduced from the fluorescence emission at 530 nm (green) and RNA content from that at 640 nm (red) as measured in a cytofluorimeter (Model 50H, Ortho Diagnostic Systems Inc., Westwood, Mass., USA) with illumination from an 8 w argon ion laser (Lexel Corp., Palo Alto, Calif., USA). The distributions were stored on a disc on a BBC microcomputer (Model B, Acorn Electronics, Cambridge, England).

Cell viability in 72 h cultures

The trypan blue exclusion test was applied cells which had been cultured for 72 h with diclofenac or fenclofenac at concentrations of 400 μg/ml. Trypan blue (50 μl of 0.05% solution) was added to 50 μl of the cell suspension and the cells taking up the dye were counted using a haemocytometer.

EXAMPLE 1

Lymphocyte activation measured by volume spectroscopy of 24 h cultures

Figure 1A:
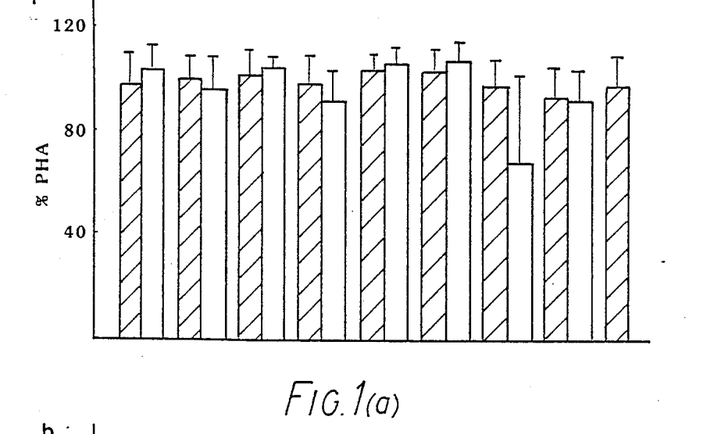
FIGS. 1(a) and 1(b) are each a block diagram showing the effect of he non-steroidal anti-inflammatory drugs used in the initial screening experiments on lymphocyte activation, measured by volume spectroscopy of 24 h phytohaemagglutinin(PHA)-stimulated cultures of lymphocytes from five normal volunteers. P is the percentage of responding cells and b the incremental growth rate of the responding cells. The left-hand columns describe the results with the drug at a concentration within the therapeutic range: the right-hand columns relate to results at a 10-fold greater concentration. The numerals under the horizontal axes indicate the following drugs: 1, ketoprofen; 2, fenbufen; 3, zomepirac; 4, sulindac; 5, indomehhacin; 6, mefenamic acid; 7, fenclofenac; 8, azapropazone; 9, salicylic acid.
Figure 1B:
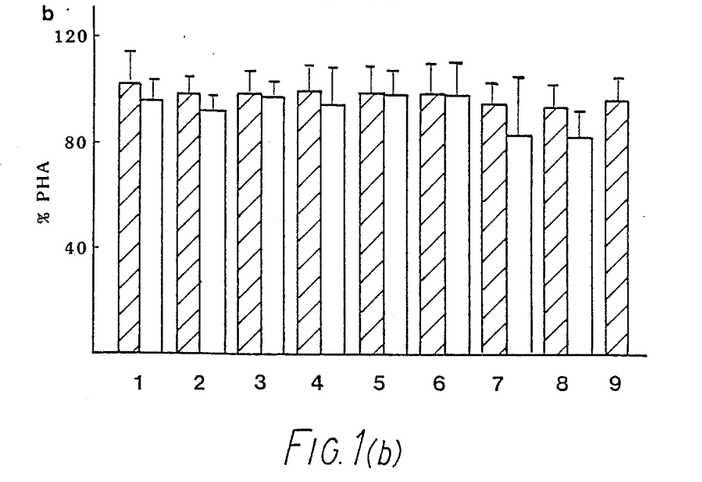
Figure 2A:
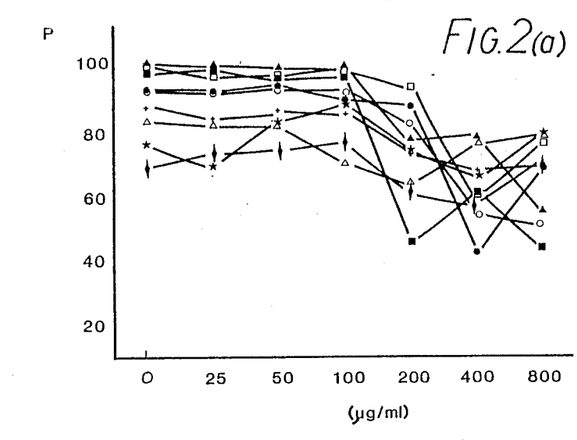
FIGS. 2(a), 2(c) and 2(b), 2(d) are graphs showing the effect of fenclofenac and diclofenac, respectively on lymphocyte activation, measured by volume spectroscopy of PHA-stimulated cultures, of lymphocytes from 9 normal volunteers. P is the percentage of responding cells and b is their incremental growth rate.
Figure 2B:
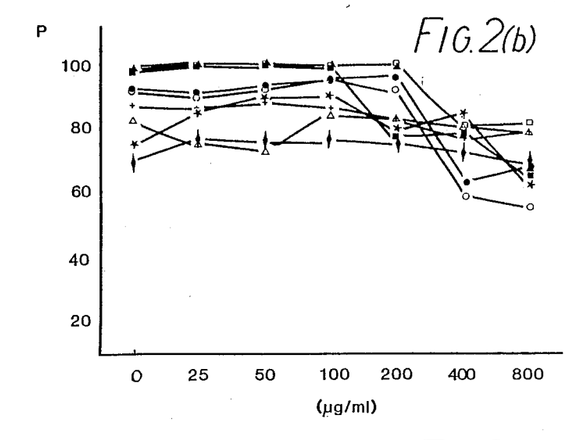
Figure 2C:
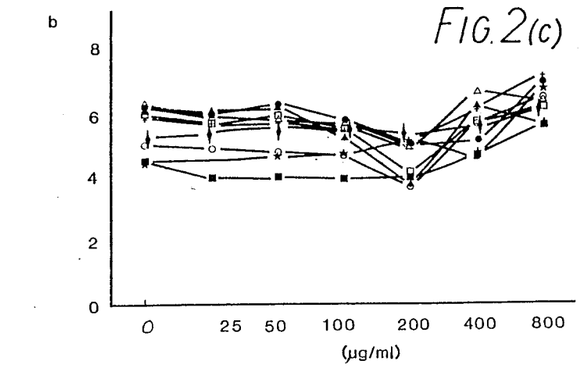
Figure 2D:
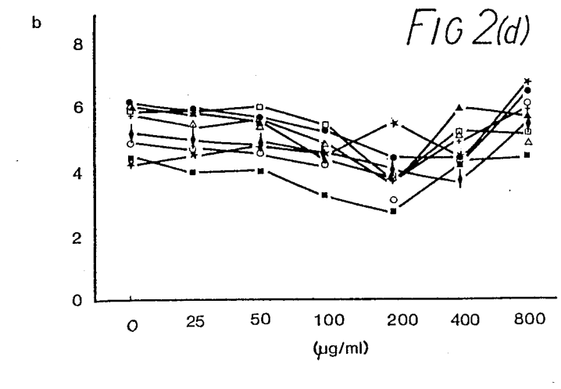

The initial screening of the representatives of seven chemical groups of non-steroidal anti-inflammatory drugs showed that fenclofenac at a concentration of 800 μg/ml (therapeutic blood level, 50–200 μg/ml) suppressed the percentage of cells responding to mitogen stimulation with phytohaemagglutinin and that fenclofenac at this concentration and azaproazone at 500 μg/ml (therapeutic blood levels <90 μg/ml) had a slight suppressive effect on the incremental growth rate (FIG. 1). None of the drugs enhanced the PHA stimulatory effect above that of the drug free control.

In the more detailed studies on phenylacetic acid derivatives, fenclofenac at concentrations greater than 100 μg/ml and diclofenac at concentrations greater than 200 μg/ml (therapeutic blood levels 0.7–1.1 μg/ml) suppressed the percentage of cells responding to mitogen stimulation by phytohaemagglutinin. Both drugs at concentrations greater than 100 μg/ml suppressed the incremental growth rate of the cells (FIG. 2), but to a lesser extent: the apparent increase at 400–800 μg/ml is thought to be due to toxic swelling of the cells.

EXAMPLE 2

Replicative growth measured by liquid scintillation of 72 h cultures

Figure 3:
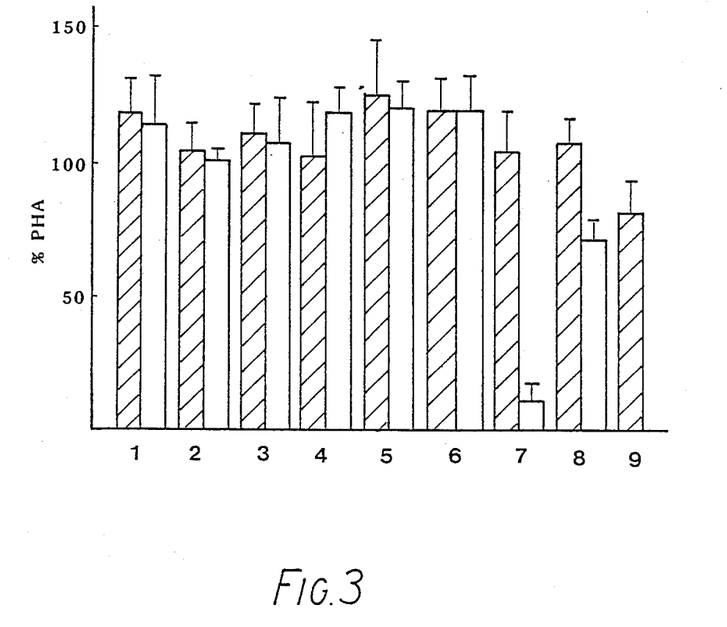
FIG. 3 is a block diagram showing the effect of non-steroidal anti-inflammatory drugs in the initial screening experiments on replicative growth, measured by tritiated thymidine ($^3$H-TdR) uptake by PHA-stimulated lymphocytes from 5 normal volunteers after culture for 72 h.

The initial screening of the representatives of seven chemical groups of non-steroidal anti-inflammatory drugs showed that fenclofenac at a concentration of 800 μg/ml greatly suppressed the replicative growth of the mitogen stimulated lymphocytes. Azapropazone at a concentration of 500 μg/ml had some effect and salicylic acid at a concentration of 300 μg/ml a less marked effect. Ketoprofen, sulindac, mefenamic acid and indomethacin enhanced the uptake of $^3$H-thymidine (FIG. 3).

Figure 4A:
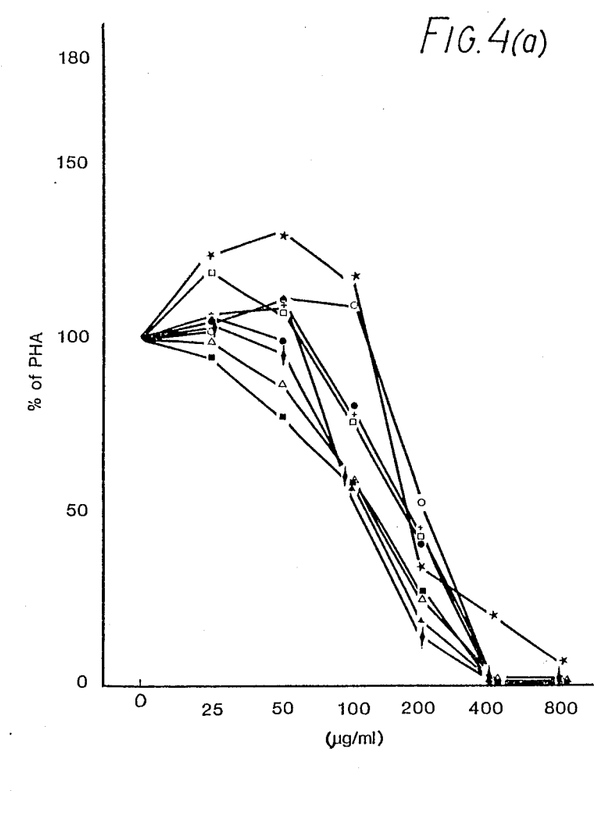
FIGS. 4(a) and 4(b) are each graphs showing the effect of fenclofenac and diclofenac, respectively on replicative growth, measured by uptake of $^3$H-TdR in PHA-stimulated lymphocytes from 9 normal volunteers cultured for 72 h.
Figure 4B:
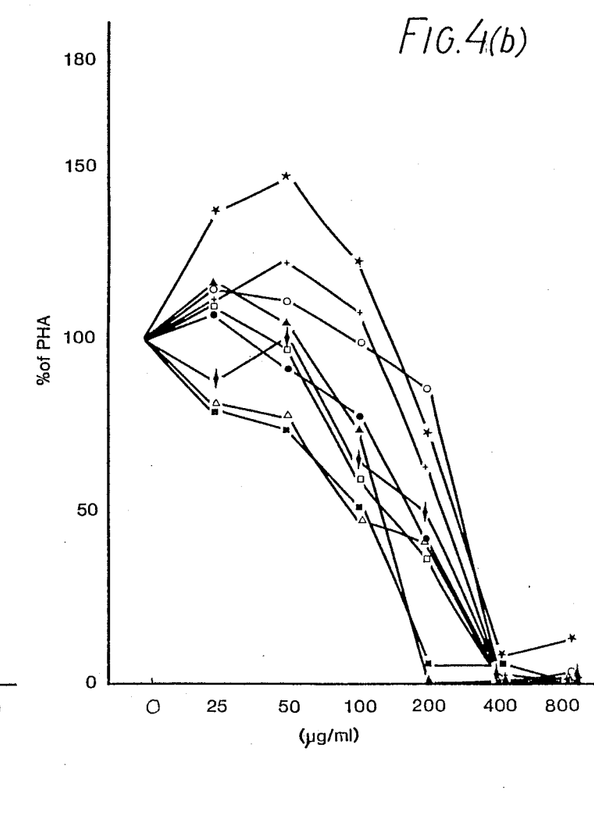

In the more detailed studies on fenclofenac and diclofenac, both drugs were seen to suppress replicative growth of mitogen stimulated lymphocytes at concentrations greater than 50–100 μg/ml in the majority of the subjects in a dose dependant manner (FIG. 4).

EXAMPLE 3

The effect of adding diclorfenac and fenclofenac at 1, 2, 4, 6, 8, 12, 24 and 48 h after the start of mitogen stimulated cultures was studied. These delayed additions showed the same pattern of suppression of replicative growth of the lymphocytes as addition of the drugs at the start of the culture. When lymphocytes were grown for 24 h in medium containing PHA and fenclofenac (200 μg/ml), then washed and finally grown for a further 48 h with PHA alone there was no suppression of replicative growth of the lymphocytes as shown in Table 2.

TABLE 2

The effect of culturing lymphocytes with fenclofenac ± phytohaemagglutinin (PHA) for 24 h followed by culture for a further 48 h with PHA alone

| | Subject 1 | | | Subject 2 | | |
|---|---|---|---|---|---|---|
| Test | Counts per minute | % of Control /PHA | % of PHA /PHA | Counts per minute | % of Control /PHA | % of PHA /PHA |
| Control/Control | 1685 ± 439 | | | 1079 ± 232 | | |
| Control/PHA | 46517 ± 5350 | | | 70606 ± 1795 | | |
| PHA/PHA | 58283 ± 2720 | | | 83083 ± 4502 | | |
| 200 μg/ml Fenclofenac DRUG/DRUG | 1627 ± 321 | | | 875 ± 246 | | |
| 200 μg/ml Fenclofenac DRUG/PHA | 47884 ± 3347 | 103 | | 74136 ± 2910 | 105 | |
| 200 μg/ml Fenclofenac DRUG + PHA/PHA | 58734 ± 5510 | | 101 | 84934 ± 5558 | | 102 |

EXAMPLE 4

Flow cytofluorimetry

Figure 5A:
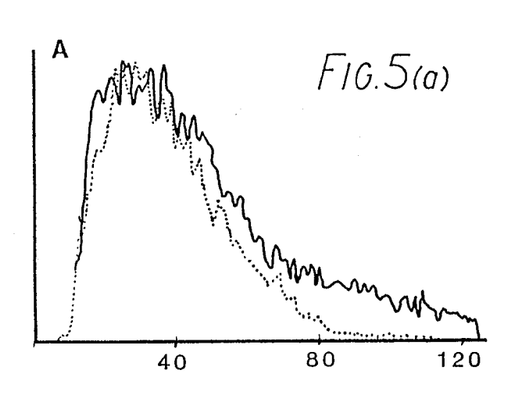
Figure 5B:
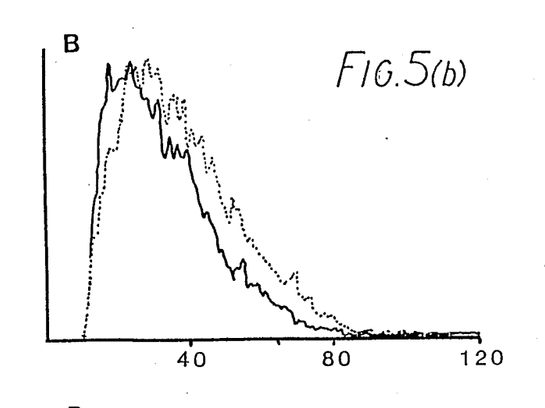
Figure 5C:
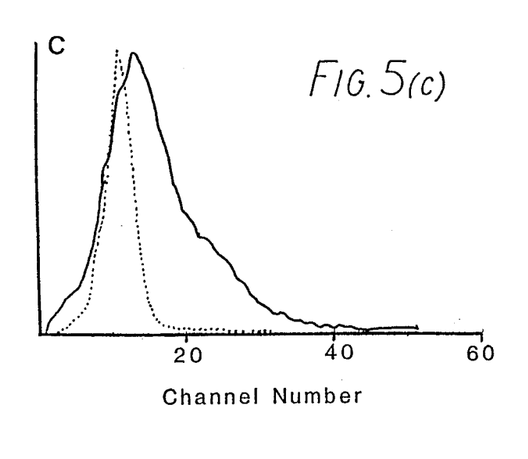
Figure 5D:
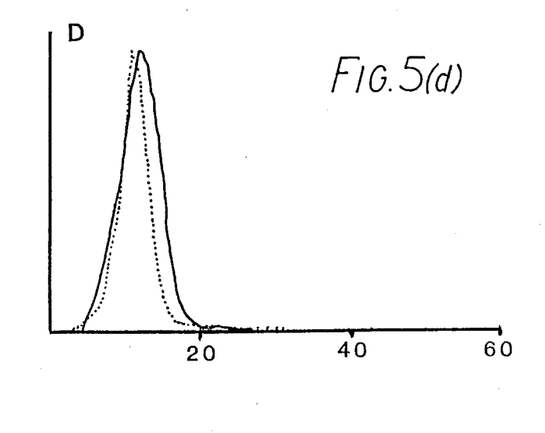

The RNA ad DNA content of individual cells was measured by flow cytofluorimetry at 24 and 72 h. the increase in RNA content with PHA stimulation of the cells was not reduced by 10 μg/ml of fenclofenac, was slightly reduced by 100 μg/ml and was totally suppressed by 500 μg/ml when compared with drug free PHA stimulated cultures at 24 and 72 h. There was little effect on the DNA content of the cells at 24 h, but at 72 h there was total suppression by 500 μg/ml of fenclofeac (FIG. 5).

EXAMPLE 5

Cell Viability

There was 98% viability of PHA stimulated lymphocytes grown for 72 h in the present of 400 μg/ml fenclofenac or 400 μg/ml diclofenac, as measured by the Trypan blue exclusion test.

EXAMPLE 6

Comparison of fenclofenac and ortho-chlorophenylacetic acid

Figure 6:
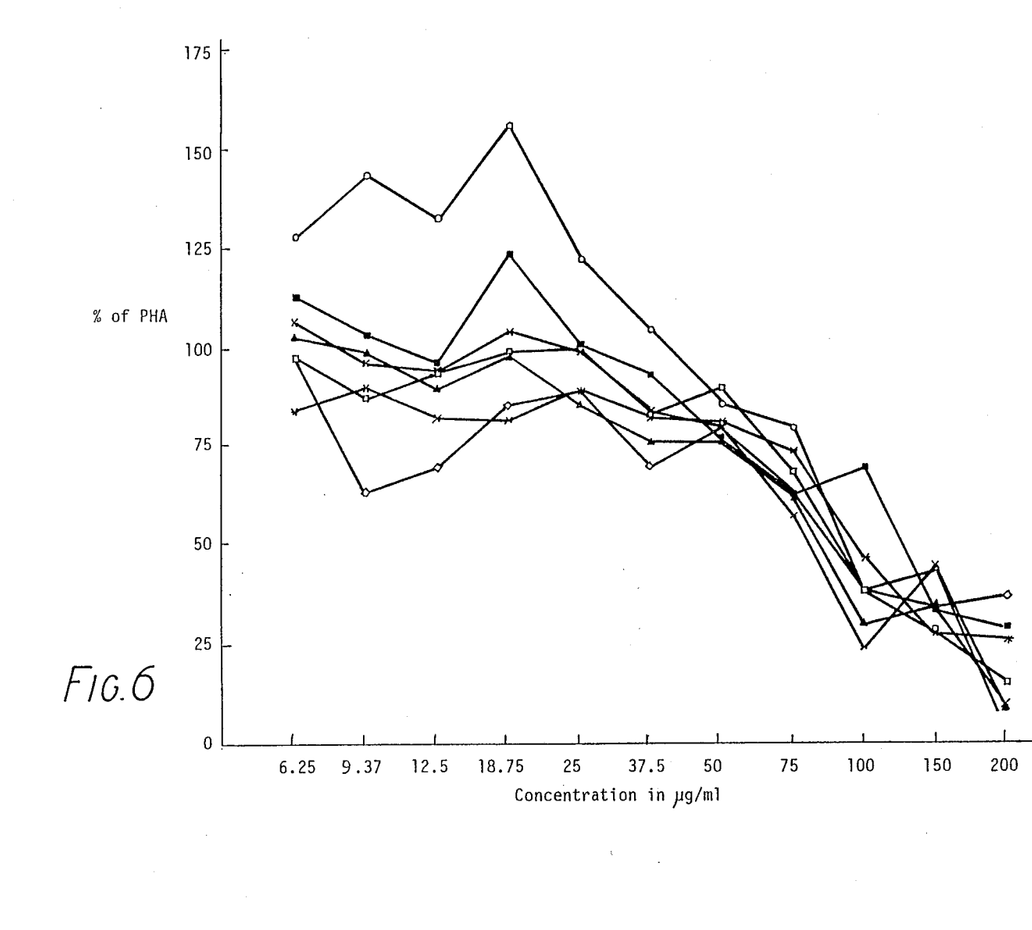
FIGS. 6 and 7 are each a graph similar to those of FIG. 4 showing the effects on replicative growth of fenclofenac and ortho-chlorophenylacetic acid respectively in suppressing the proliferation of human lymphocytes in vitro.
Figure 7:
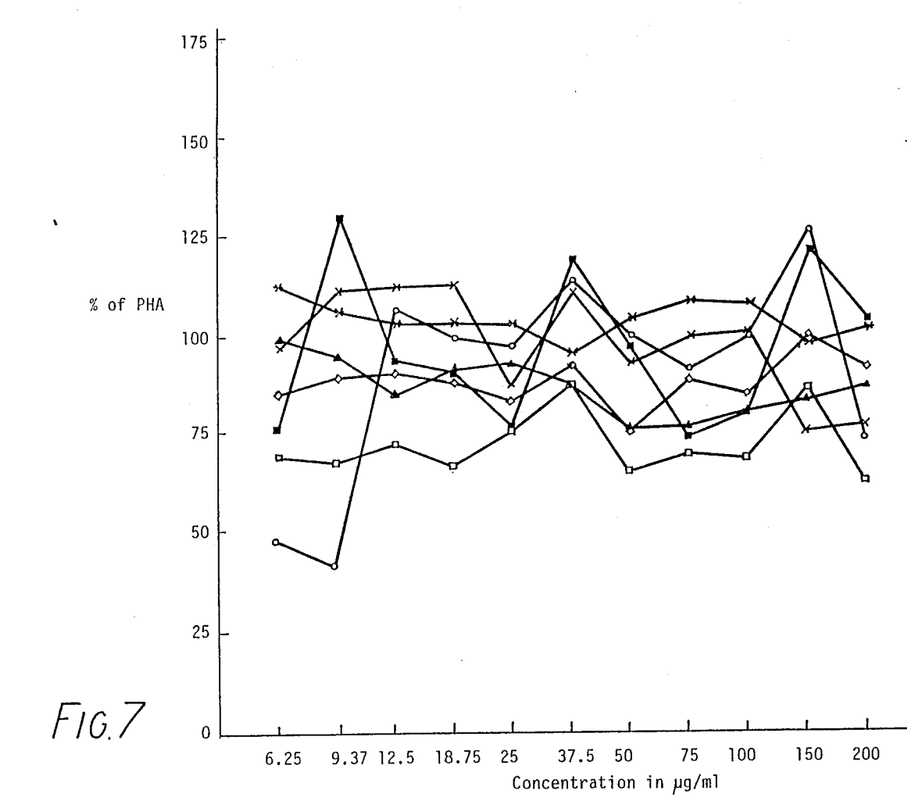

The effect of ortho-chlorophenylacetic acid, the base from which the analogue fenclofenac is derived, on the proliferation of norma human lymphocytes in vitro was tested along with fenclofenac for comparison. Both drugs were dissolved in absolute ethanol 28.0 mg in 1.0 ml ethanol and diluted with tissue culture medium RPMI 1640 for addition to the tissue culture wells. Each well contained 50 μl of cell suspension $4 \times 10^6$/ml, 50 μl drug dilution, 25 μl autologous plasma and 50 μl PHA at an optimum stimulating concentration of 1.14 μg HA16/ml RPMI 1640. The plates were incubated at 37° C. in 5% $CO_2$. Both compounds were tested over the concentration range of 6.25 μg/ml to 200 μg/ml and the replicative growth of the lymphocytes was measured by tritiated thymidine uptake at 72 h. The results are shown in FIG. 6 for fenclofenac and in FIG. 7 for ortho-chlorophenylacetic acid.

EXAMPLE 7

Figure 8:
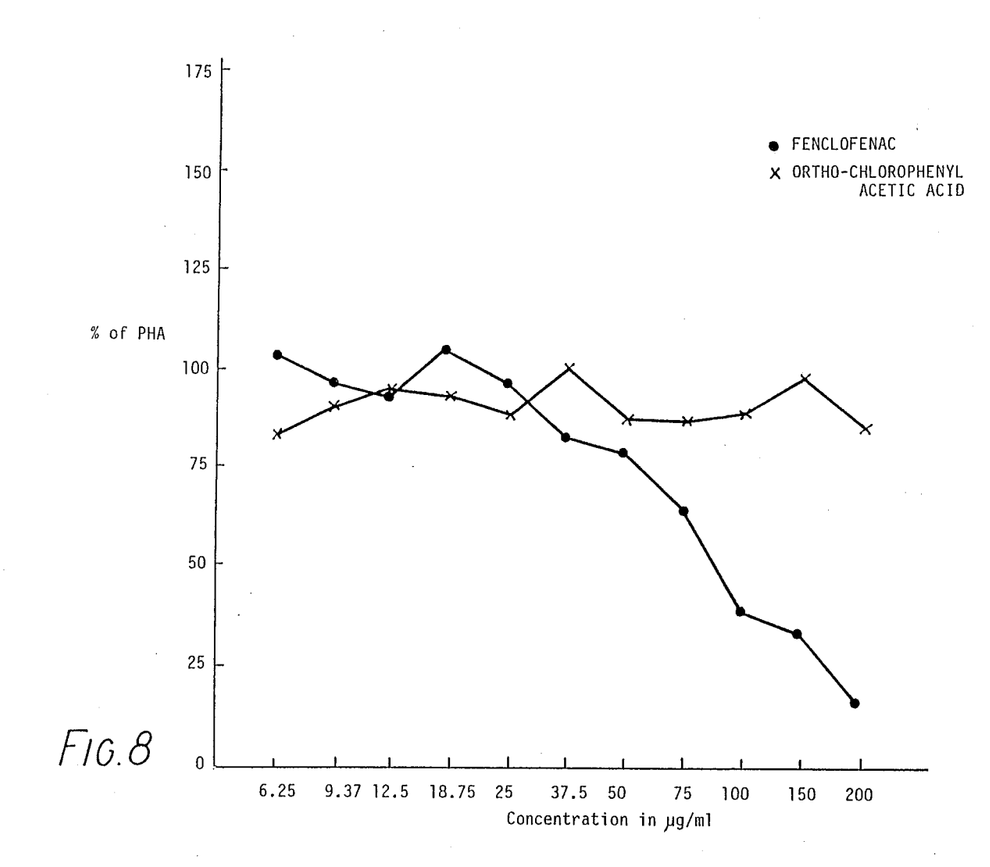
FIG. 8 is a graph similar to that of FIGS. 6 and 7 showing the mean of the results from seven subjects at each concentration of fenclofenac and orthochlorophenylacetic acid.

The mean of the results of the dose responses on lymphocytes from seven normal volunteers The mean of the results from seven subjects of the effect of fenclofenac is compared with the means of the results from seven subjects of the effect of ortho-chlorophenylacetic acid on the replicative growth of the lymphocytes as measured by the uptake of tritiated thymidine at 72 hours, FIG. 8. Each concentration of drug was set up in triplicate and the mean of the counts for the three wells was taken and calculated as a percentage of the results from the PHA stimulated wells with no drug added.

Diclofenac and fenclofenac, members of the phenylacetic acid derivative group, suppress mitogen stimulated lymphocytes in vitro at concentrations greater than 50–100 μg/ml. Although this concentration lies within the therapeutic range of blood levels for fenclofenac of 50–200 μg/ml, it is 100-fold greater than the therapeutic range of blood levels for diclofenac of 0.7–1.1 μg/ml. It is interesting that these two drugs in the same chemical group are equally potent in the in vitro test systems but have different potencies for their in vivo clinical effect. Both are well absorbed from the gastrointestinal tract and are 99.5% bound to serum proteins, the peak plasma concentrations are around 2–3 h [Makela, A. L. et al. *Eur. J. Clin. Pharmacol* 25, 381–388 (1983)], [Fowler, P. D. et al., *Eur. J. Clin. Pharmacol.*, 25, 389–394 (1983)].

The elimination half life of diclofenac is very short at 3–5 h [Fowler et al., (1983)] while that of fenclofenac is much longer at 25.4±7.9 h [Makela et al., (1983)]. Both drugs enter the synovial fluid fairly rapidly and their levels in the synovial fluid exceed the plasma levels from 5 h [Makela et al., (1983); Fowler et al., (1983)]. The maintenance of a significant level of the drugs in the synovial fluid after the level has fallen in the blood is thought to be responsible for the extended therapeutic effect especially in the case of diclofenac which has a short elimination half life [Fowler et al., (1983)]. Diclofenac is metabolised by hydroxylation at the ara position of the phenyl amino ring and is mainly excreted in the urine. The levels of the metabolites in the blood and synovial fluid decline more slowly than the drug concentrations and as the 4'-hydroxy meaabolite is therapeutically active this may also add to the extended therapeutic effect of diclofenac [Fowler et al., (1983)].

Hydroxylation of fenclofenac at the para position is prevented by a chloride atom substitution and the drug is eliminated by conjugation with glucuronic acid and excretion in the urine. The therapeutic activity is thought to be due to the parent drug [Makela et al., (1983)].

There have been few studies in which the therapeutic potency of fenclofenac and diclofenac have been compared directly. Bedi, S. S. et al. [*Brit. J. Rheumatol.*, 23, 214,219 (1984)] have found that the daily dose for maintenance therapy in rheumatoid arthritis is 1200 mg for fenclofenac and 150 mg for diclofenac. This difference in potency cannot be readily explained from the pharmacokinetics of the drugs. Diclofenac is a very potent cyclooxygenase inhibitor relative to certain non-steroidal anti-inflammatory drugs in other chemical groups (Ku, E. C. et al., [*Seminars in Arthritis and Rheumatism,* 15, 2, Suppl. 1, 36–41 (1985)], but reliable figures for the activity of fenclofenac in this respect cannot be obtained. There is thus no obvious explanation for the difference in therapeutic potency between these two phenylacetic acid derivative non-steroidal anti-inflammatory drugs.

Goodwin, J. S., [*Amer. J. Med.,* 77 Special issues, Oct. 15th, 7–15 (1984)] has suggested that the therapeutic effect of non-steroidal anti-inflammatory drugs is not due to cyclooxygenase inhibition alone and this would appear to be true in the present in vitro system. Prostaglandin $E_2$ inhibits tritiated thymidine incorporation into human peripheral blood mononuclear cells when added to phytohaemagglutinin stimulated cultures. Prostaglandin $E_2$ is produced in phytohaemagglutin in stimulated cultures of human peripheral blood mononuclear cells in amounts that when added exogenously cause inhibition of mitogen stimulation [Goodwin, (1984)]. Cyclooxygenase inhibitors would therefore be expected to increase the uptake of tritiated thymidine into the cells by inhibiting the production of prostaglandin $E_2$ by the monocytes in the cultures. This would explain the stimulatory effect of indomethacin, ketoprofen, sulindac and mefenamic acid. At lower concentration, diclofenac and fenclofenac were also stimulatory in some of the subjects in the detailed studies. The inhibitory effect of the higher concentrations of fenclofenac and diclofenac must be due to other mechanisms.

Dinarello, C. A. et al., [*Int. J. Immunopharmac.,* 6, 1, 43–50 (1984)] have shown that lipoxygenase inhibitors inhibit the production of Interleukin 1 from human monocytes when added at the start of an in vitro culture, but when they are added 1 h after the start of the culture they have no effect. Diclofenac and fenclofenac added at 1 and 2 h after the start of the culture were just as suppressive as when added at the beginning of the culture. Therefore they do not appear to exert their effect by inhibiting Interleukin 1 production by monocytes. They do not appear to have much effect on any stage of activation of lymphocytes since addition of the drugs up to 48 h after the start of the culture produced similar inhibition of replicative growth as drugs added at the start of the culture. Also when the cells were grown for 24 h in the presence of drug and then for a further 48 h without drug there was no suppression of replicative growth. The suppressive effect of the phenylacetic acid derivative drugs on the PHA-stimulated lymphocytes would therefore appear to take place after activation. Whatever the basis of this effect, it is not cytotoxic since the drugs do not interfere with the Trypan blue exclusion test performed at 72 h.

What I claim is:

1. A method of suppressing the activity of lymphocytes in a subject requiring such suppression comprising administering to said subject, a therapeutically effective amount of fenclofenac.

2. A method of treating chronic inflammatory diseases in a human or animal comprising administering to said human or animal a therapeutically effective amount of fenclofenac.

3. A method of treating hypersensitivity reactions and conditions in a subject comprising administering to said subject a therapeutically effective amount of fenclofenac.

4. A method of suppressing the activity of lymphocytes in a human or animal requiring such suppression comprising administering to said human or animal a therapeutically effective amount of fenclofenac.

5. A method as claimed in claim 1, wherein the medicament is in a form for release in the terminal ileum or colon.

* * * * *